United States Patent
Wang

(10) Patent No.: US 12,000,839 B2
(45) Date of Patent: Jun. 4, 2024

(54) METHODS FOR CHARACTERIZING DISULFIDE BONDS

(71) Applicant: Regeneron Pharmaceuticals, Inc., Tarrytown, NY (US)

(72) Inventor: Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/154,401

(22) Filed: Jan. 13, 2023

(65) Prior Publication Data

US 2023/0280354 A1     Sep. 7, 2023

Related U.S. Application Data

(62) Division of application No. 16/745,006, filed on Jan. 16, 2020, now Pat. No. 11,579,150.

(60) Provisional application No. 62/792,994, filed on Jan. 16, 2019.

(51) Int. Cl.

| | | |
|---|---|---|
| *G01N 33/68* | (2006.01) | |
| *A61K 39/395* | (2006.01) | |
| *G01N 1/28* | (2006.01) | |
| *G01N 30/72* | (2006.01) | |
| G01N 30/02 | (2006.01) | |
| G01N 30/88 | (2006.01) | |

(52) U.S. Cl.
CPC ....... *G01N 33/6848* (2013.01); *A61K 39/395* (2013.01); *G01N 1/28* (2013.01); *G01N 30/7233* (2013.01); *G01N 33/6854* (2013.01); G01N 2030/027 (2013.01); G01N 2030/8831 (2013.01); G01N 2458/15 (2013.01)

(58) Field of Classification Search
None
See application file for complete search history.

(56) References Cited

U.S. PATENT DOCUMENTS

| | | |
|---|---|---|
| 9,835,629 B2 | 12/2017 | Rogers et al. |
| 11,579,150 B2 | 2/2023 | Wang |
| 11,674,968 B2 | 6/2023 | E et al. |
| 2013/0309689 A1 | 11/2013 | Rogers et al. |

(Continued)

FOREIGN PATENT DOCUMENTS

| | | |
|---|---|---|
| WO | 2016/018978 A1 | 2/2016 |
| WO | 2018/170981 A1 | 9/2018 |

OTHER PUBLICATIONS

Ambrogelly et al., Analytical comparability study of recombinant monoclonal antibody therapeutics. MAbs. May/Jun. 2018;10(4):513-538.

(Continued)

*Primary Examiner* — Xiaoyun R Xu
(74) *Attorney, Agent, or Firm* — McCarter & English, LLP

(57) ABSTRACT

Compositions and methods for analyzing disulfide bonds are provided. An exemplary method includes preparing peptide standards having no disulfide bonds, scrambled disulfide bond peptide standards, and native disulfide bond peptide standards according to the sequence of the region of the protein drug product that includes the disulfide bond, digesting a sample of protein drug product into peptides, separating the protein drug product peptides, analyzing the protein drug product peptides and the peptide standards, identifying scrambled and native disulfide bond peptides by retention time, and quantifying the level of scrambled disulfide bond peptides.

18 Claims, 17 Drawing Sheets

Specification includes a Sequence Listing.

(56) References Cited

U.S. PATENT DOCUMENTS

| | | |
|---|---|---|
| 2018/0106815 A1 | 4/2018 | Barnidge et al. |
| 2020/0225243 A1 | 7/2020 | Wang |
| 2023/0273216 A1 | 8/2023 | E et al. |

OTHER PUBLICATIONS

Cao et al., Characterization and analysis of scFv—IgG bispecific antibody size variants. MAbs. Nov.-Dec. 2018;10(8):1236-1247.

Guan et al., Direct mass spectrometric characterization of disulfide linkages. MAbs. May/Jun. 2018;10(4):572-582.

Van Den Bremer et al., Cysteine-SILAC Mass Spectrometry Enabling the Identification and Quantitation of Scrambled Interchain Disulfide Bonds: Preservation of Native Heavy-Light Chain Pairing in Bispecific IgGs Generated by Controlled Fab-arm Exchange. Anal Chem. Oct. 17, 2017;89(20):10873-10882.

International Search Report and Written Opinion for Application No. PCT/US2020/013910, dated Apr. 28, 2020, 11 pages.

U.S. Appl. No. 16/745,006, filed Jan. 16, 2020, U.S. Pat. No. 11,579,150.

U.S. Appl. No. 16/745,020, filed Jan. 16, 2020, U.S. Pat. No. 11,674,968.

U.S. Appl. No. 18/142,193, filed May 2, 2023, 2023-0273216.

Araki et al., Redox Sensitivities of Global Cellular Cysteine Residues under Reductive and Oxidative Stress. J Proteome Res. Aug. 5, 2016;15(8):2548-59.

Bouhallab et al., Copper-catalyzed formation of disulfide-linked dimer of bovine B-lactoglobulin. Lait. 2004;84(6):517-25.

Clark et al., Simple approach to assign disulfide connectivity using extracted ion chromatograms of electron transfer dissociation spectra. Anal Chem. Jan. 15, 2013;85(2):1192-9.

Eliuk et al., Evolution of Orbitrap Mass Spectrometry Instrumentation. Annu Rev Anal Chem (Palo Alto Calif). 2015;8:61-80.

Feng et al., Global analysis of protein structural changes in complex proteomes. Nat Biotechnol. Oct. 2014;32(10):1036-44.

Furuki et al., Determination of thiol-to-protein ratio and drug-to-antibody ratio by in-line size exclusion chromatography with post-column reaction. Anal Biochem. Jun. 15, 2017;527:33-44.

Giron et al., Cysteine tagging for MS-based proteomics. Mass Spectrom Rev. May-Jun. 2011;30(3):366-95.

Guo et al., Counting sulfhydryls and disulfide bonds in peptides and proteins using mercurial ions as an MS-tag. J Am Soc Mass Spectrom. Aug. 2008;19(8):1108-13.

Kita, Mass spectrometry based experimental strategies to characterize native and non-native disulfide bonds in cysteine-rich protein therapeutics. Doctoral Dissertation, University of Massachusetts Amherst. Nov. 2014, 112 pages.

Lakbub et al., Disulfide Bond Characterization of Endogenous IgG3 Monoclonal Antibodies Using LC-MS: an Investigation of IgG3 Disulfide-mediated Isoforms. Anal Methods. Aug. 21, 2016;8(31):6046-6055.

Lakbub et al., Recent mass spectrometry-based techniques and considerations for disulfide bond characterization in proteins. Anal Bioanal Chem. Apr. 2018;410(10):2467-2484.

Li et al., Disulfide bond assignment of an IgG1 monoclonal antibody by LC-MS with post-column partial reduction. Anal Biochem. May 2013;436(2):93-100.

Li et al., Liquid chromatography and mass spectrometry with post-column partial reduction for the analysis of native and scrambled disulfide bonds. Anal Biochem. Aug. 15, 2013;439(2):184-6.

Linderholm et al., Immunoglobulin Fc-Fusion Proteins Part 1: Their Design and Manufacture. Retrieved online at: https://bioprocessintl.com/manufacturing/monoclonal-antibodies/immunoglobulin-fc-fusion-proteins-part-1-design-manufacture/. 12 pages, Oct. 16, 2014.

Liu et al., Characterization of free thiol variants of an IgG1 by reversed phase ultra high pressure liquid chromatography coupled with mass spectrometry. J Pharm Biomed Anal. May 10, 2015;109:142-9.

Moritz et al., Assessment of disulfide and hinge modifications in monoclonal antibodies. Electrophoresis. Mar. 2017;38(6):769-785.

Pan et al., Mass spectrometry-based quantitative proteomics for dissecting multiplexed redox cysteine modifications in nitric oxide-protected cardiomyocyte under hypoxia. Antioxid Redox Signal. Mar. 20, 2014;20(9):1365-81.

Prudent et al., The role of copper in cysteine oxidation: study of intra- and inter-molecular reactions in mass spectrometry. Metallomics. Mar. 2009;1(2):157-65.

Resemann et al., Rapid, automated characterization of disulfide bond scrambling and IgG2 isoform determination. MAbs. Nov.-Dec. 2018;10(8):1200-1213.

Seiwart et al., Differential labeling of free and disulfide-bound thiol functions in proteins. J Am Soc Mass Spectrom. Jan. 2008;19(1):1-7.

Shakir et al., Quantitative analysis of the cysteine redoxome by iodoacetyl tandem mass tags. Anal Bioanal Chem. Jun. 2017;409(15):3821-3830.

Tsai et al., Mass spectrometry-based strategies for protein disulfide bond identification. Rev Anal Chem. Aug. 9, 2013;32(4):257-68.

Wang et al., Characterization and comparison of disulfide linkages and scrambling patterns in therapeutic monoclonal antibodies: using LC-MS with electron transfer dissociation. Anal Chem. Apr. 15, 2011;83(8):3133-40.

Xiang et al., Localization and quantitation of free sulfhydryl in recombinant monoclonal antibodies by differential abeling with 12C and 13C iodoacetic acid and LC-MS analysis. Anal Chem. Oct. 1, 2009;81(19):8101-8.

Yan et al., Human IgG1 hinge fragmentation as the result of H2O2-mediated radical cleavage. J Biol Chem. Dec. 18, 2009;284(51):35390-402.

Zheng et al., The impact of glycosylation on monoclonal antibody conformation and stability. MAbs. Nov.-Dec. 2011;3(6):568-76.

International Search Report and Written Opinion for Application No. PCT/US2020/013907, dated Apr. 28, 2020, 12 pages.

U.S. Appl. No. 16/745,006, filed Jan. 16, 2020, 2020/0225243.

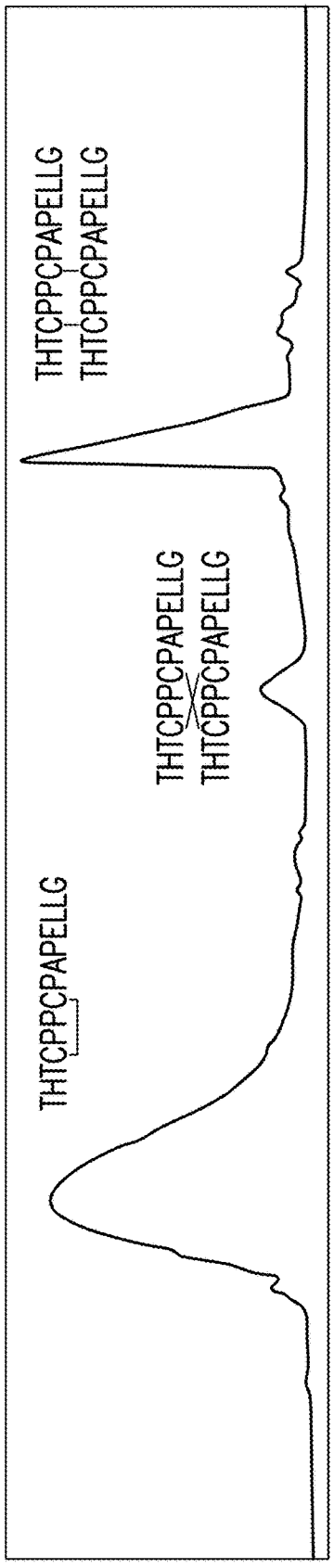
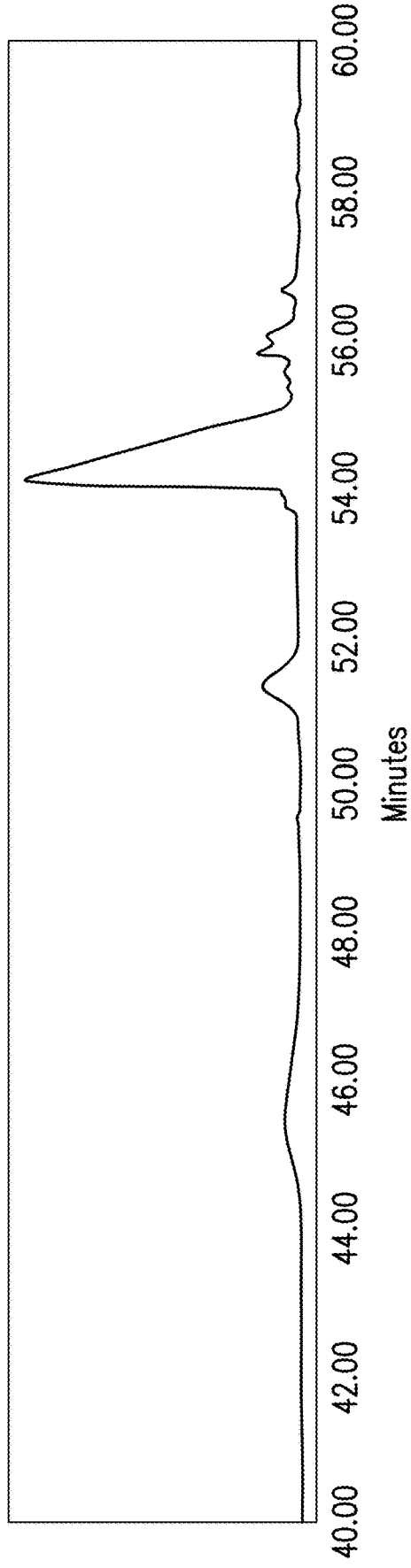
FIG.2A
FIG.2B

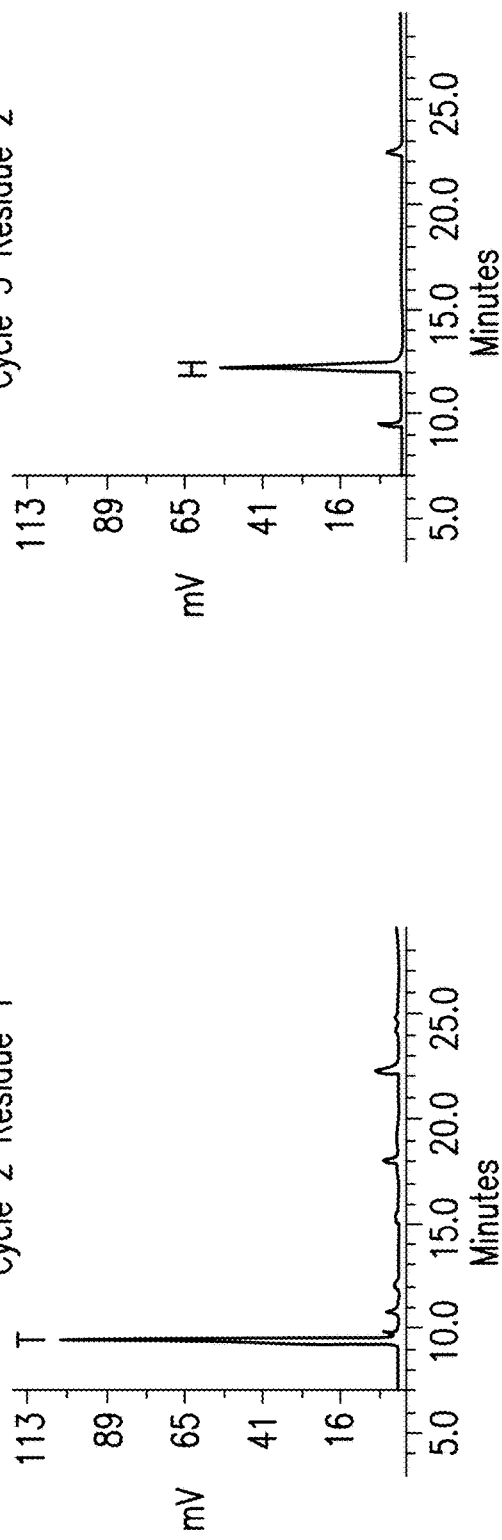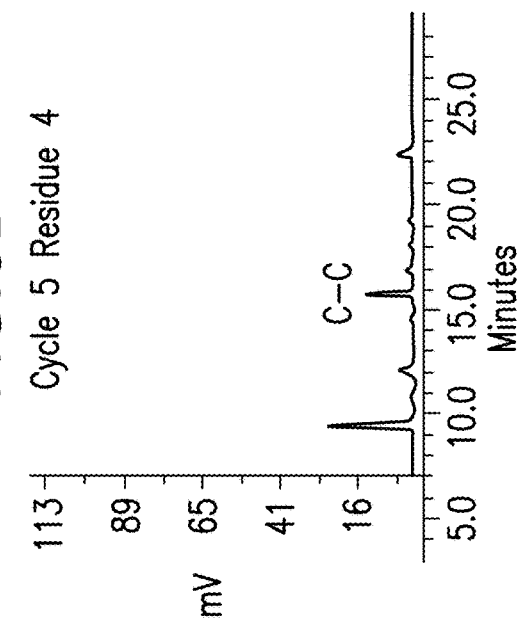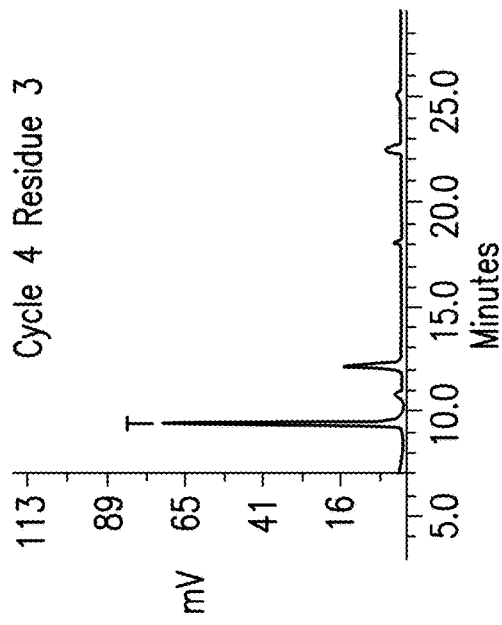
FIG.3A  FIG.3B  FIG.3C  FIG.3D

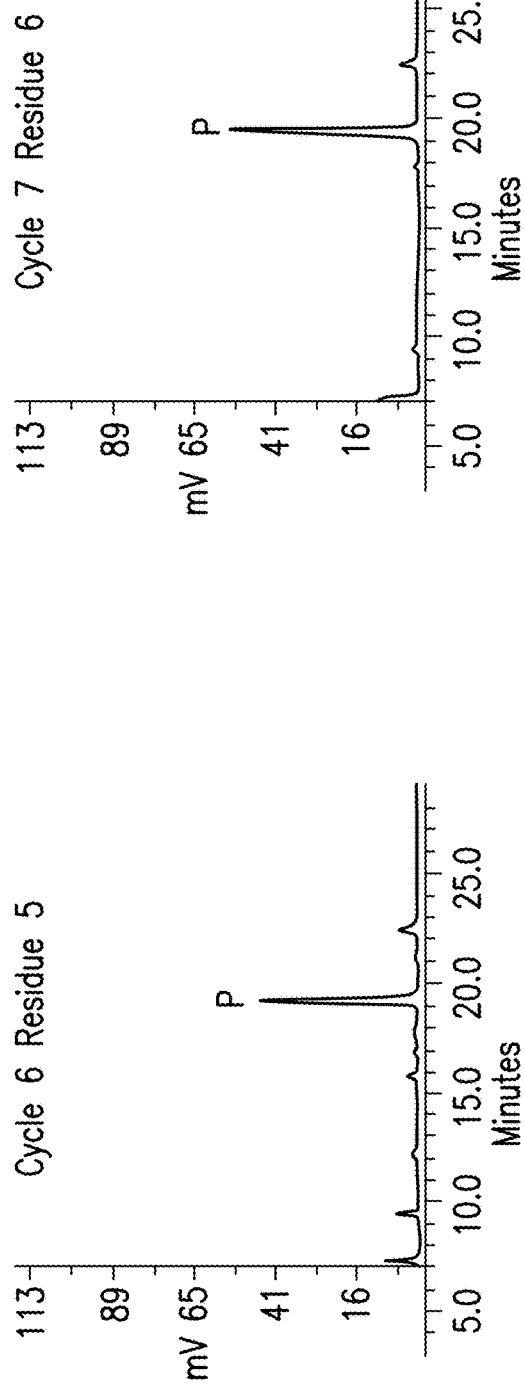
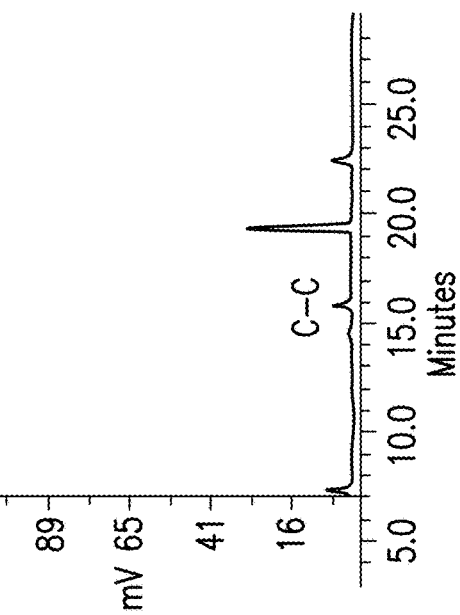
FIG. 3E
FIG. 3F
FIG. 3G

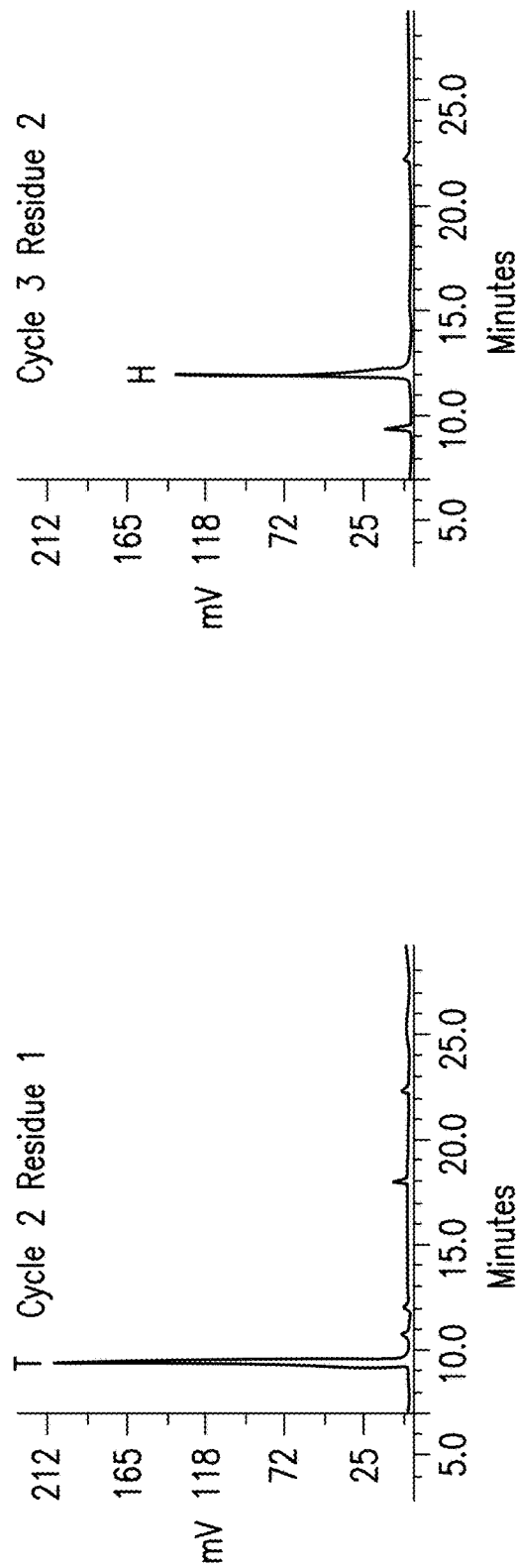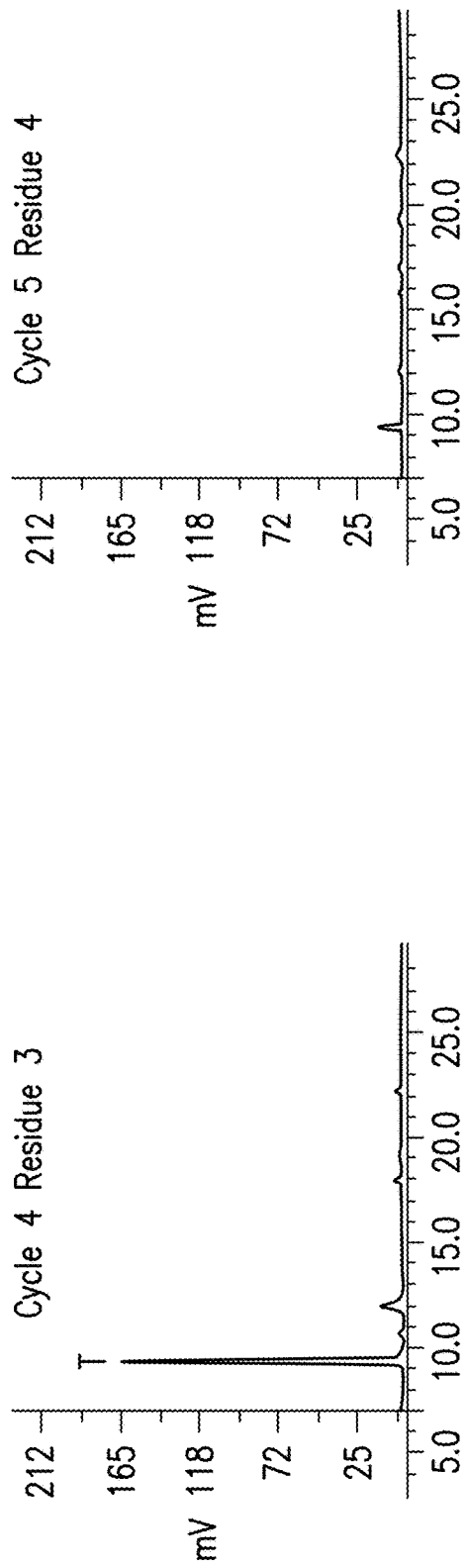

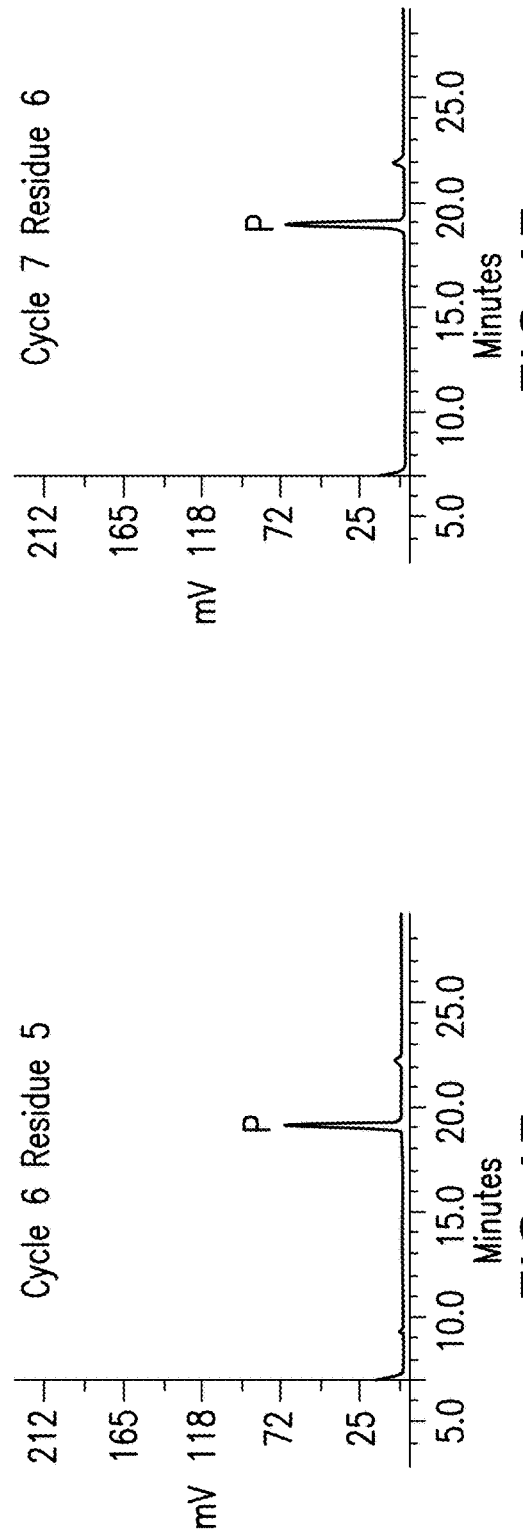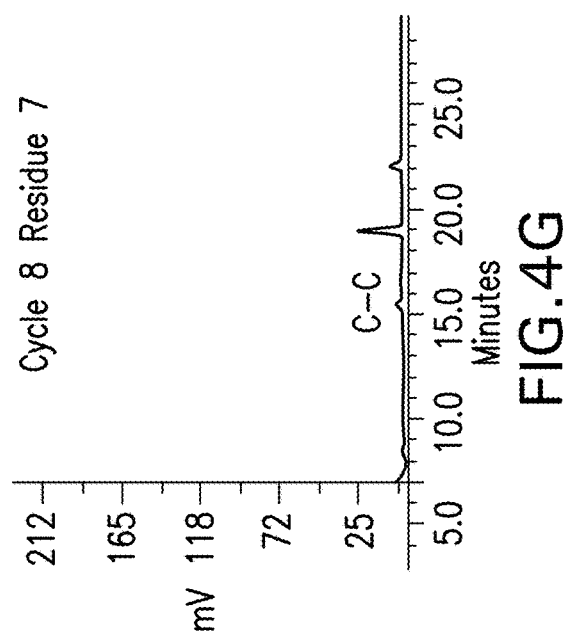
FIG.4E
FIG.4F
FIG.4G

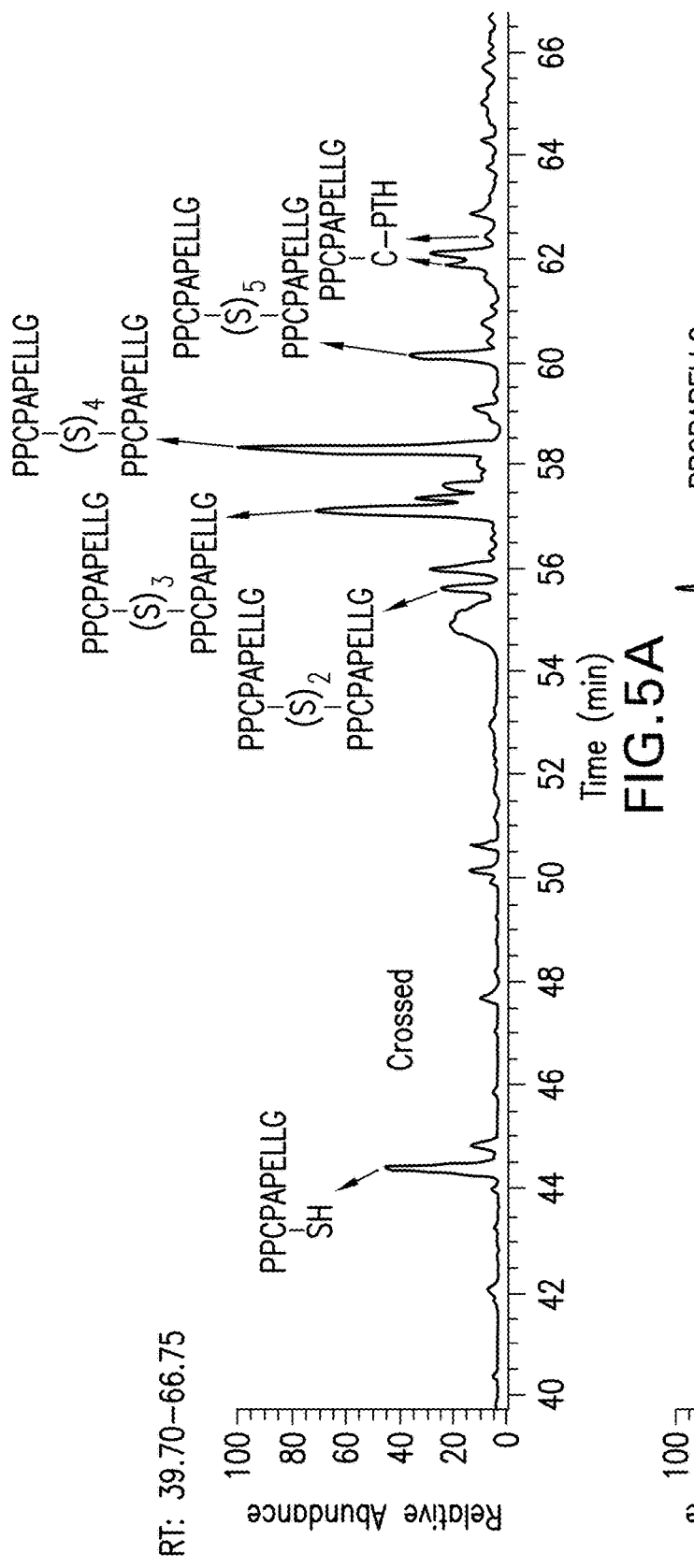
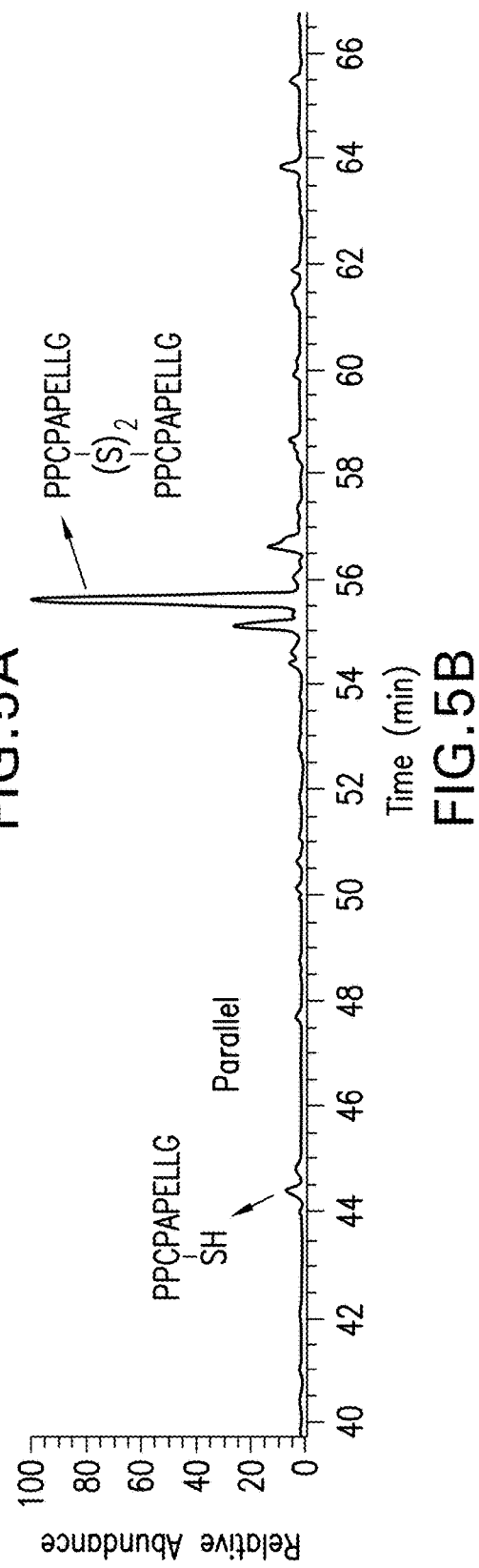

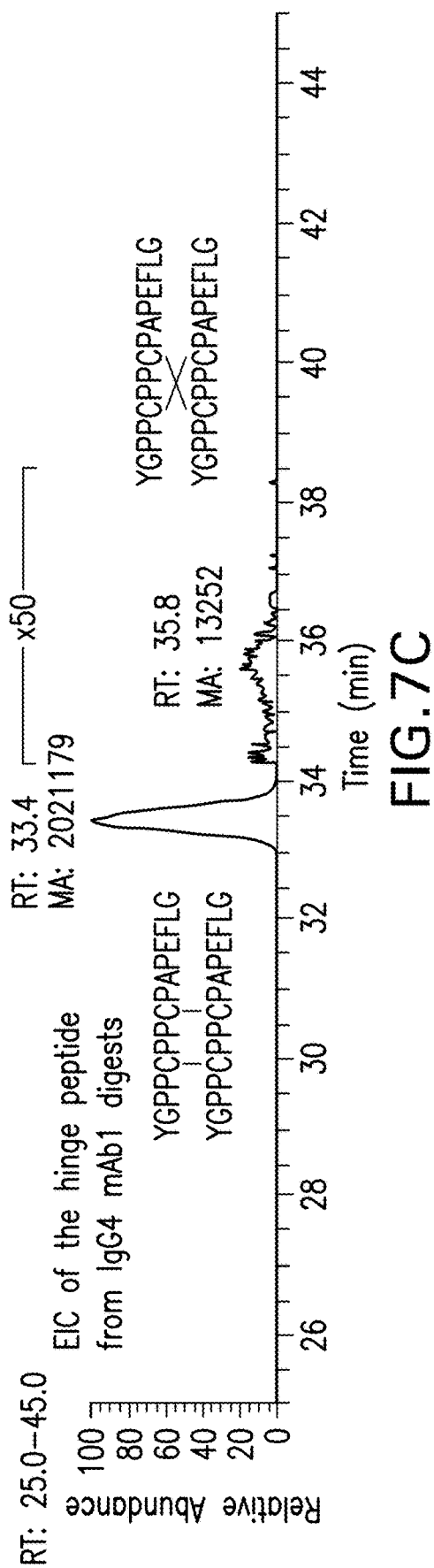

METHODS FOR CHARACTERIZING DISULFIDE BONDS

CROSS-REFERENCE TO RELATED APPLICATIONS

This application is a divisional of U.S. patent application Ser. No. 16/745,006, filed Jan. 16, 2020, which claims benefit of and priority to U.S. Provisional Patent Application No. 62/792,994, filed Jan. 16, 2019, the entire contents of each of which are incorporated herein by reference in their entirety.

REFERENCE TO SEQUENCE LISTING

The Sequence Listing submitted Jan. 13, 2023, as a text file named "10418_135975_418XX_SL", and having a size of 5,872 bytes, is hereby incorporated by reference pursuant to 37 C.F.R. § 1.52(e)(5).

TECHNICAL FIELD OF THE INVENTION

The invention is generally related to systems and methods of characterizing antibodies, in particular disulfide bonds.

BACKGROUND OF THE INVENTION

During the development of monoclonal antibodies (mAbs) from drug candidate to marketed product, issues with stability, post-translational modifications, or other changes to the antibody can occur. Alterations in antibody structure and function can cause problems such as poor shelf-life or even immunogenicity in the patient. It is therefore important to properly characterize antibody structure and monitor it throughout production. Antibody quality control and quality assurance are critical to the purity and safety of mAb products.

Disulfide bonds are important for structural integrity, stability, and biological functions of mAbs. Non-native disulfide bonds can cause changes in the structure and stability of mAbs. Binding affinity of mAbs to antigens can be affected by up to 50% if disulfide bonds are incomplete (Xiang, T., et al., Anal Chem, 81:8101-8108 (2009)). The low dissociation energy of disulfide bonds and the high flexibility of the hinge region frequently lead to modifications and cleavages at the hinge region (Moritz, B., and Stracke, J. O., Electrophoresis, 36:769-785 (2017)). In addition, administration of non-native disulfide bonded structures to humans has the potential to trigger unwanted immune responses. Analysis of disulfide bonds is therefore important for quality control assessment of mAbs. Current methods of analyzing mAb disulfide bonds are time-consuming and labor intensive.

Therefore, it is an object of the invention to provide systems and methods for characterizing monoclonal antibodies, in particular disulfide bonds in monoclonal antibodies.

SUMMARY OF THE INVENTION

Compositions and methods for characterizing disulfide bonds are provided. One embodiment provides a method for identifying scrambled disulfide bonds in a protein drug product and includes the steps of preparing peptide standards having regions of the protein drug product containing one or more disulfide bonds. The peptide standards can be made to contain each different kind of scrambled disulfide bond. For example one standard can include a crossed disulfide bond, and another standard can include an intrachain disulfide bond. FIG. 1A shows exemplary forms of disulfide bonds that can be present in the peptide standard. In one embodiment, the peptide standard contains a normal or parallel disulfide bond. Each peptide standard has a different, known liquid chromatography retention time compared to the other peptide standards. The method includes digesting a sample of protein drug product into peptides, and analyzing a sample containing protein drug product peptides and the peptide standards using a liquid chromatography tandem mass spectrometry system (LC-MS$^2$ system). Peptides detected at the retention times of the different standards are indicative to the presence in the protein drug product of the type of disulfide bond in the specific peptide standard. In one embodiment, the protein drug product is a monoclonal antibody. In other embodiments, the protein drug product is a recombinant protein, a fusion protein, or a combination thereof.

The peptide standards can be prepared using conventional techniques. For example an oxidation reaction can be used to generate disulfide bonds in the peptide standards. In one embodiment, the oxidation reaction is performed using $Cu^{2+}$.

Another embodiment provides a method of producing a protein drug product including the steps of producing the protein drug product in a cell culture and identifying scrambled disulfide bonds of the protein drug product using the method describe above. The method includes modifying one or more cell culture, purification or excipient conditions to reduce the amount of crossed hinge disulfide bonds of the protein drug product to less than 1.0%. The one or more conditions can include cell culture conditions such as temperature, pH, oxygen levels, reactive oxygen species, surfactants, or combinations thereof.

Another embodiment provides a pharmaceutical composition including monoclonal antibodies having less than 30% scrambled disulfide bonds

BRIEF DESCRIPTION OF THE DRAWINGS

FIGS. 2A-2B are chromatograms showing disulfide bond formation in peptides that were incubated with $Cu^{2+}$ overnight. The peptides were either ~0.1 µg/ml (FIG. 2A) or ~8 µg/ml (FIG. 2B). The peptides have the sequence THTCPPCPAPELLG (SEQ ID NO:1). The X axis represents time (minutes) and the Y axis represents relative abundance.

FIGS. 3A-3H are chromatograms showing the results of N-terminal analysis of the parallel hinge peptide standard. The X axes represent time (minutes) and the Y axes represent mV.

The peptide sequences are as follows: THTCPPCPAPELLG (SEQ ID NO:1), C-PTH (SEQ ID NO:2), and PPCPAPELLG (SEQ ID NO:3).

FIGS. 4A-4H are chromatograms showing the results of N-terminal analysis of the crossed hinge peptide standard. The X axes represent time (minutes) and the Y axes represent mV.

Figure 4H:
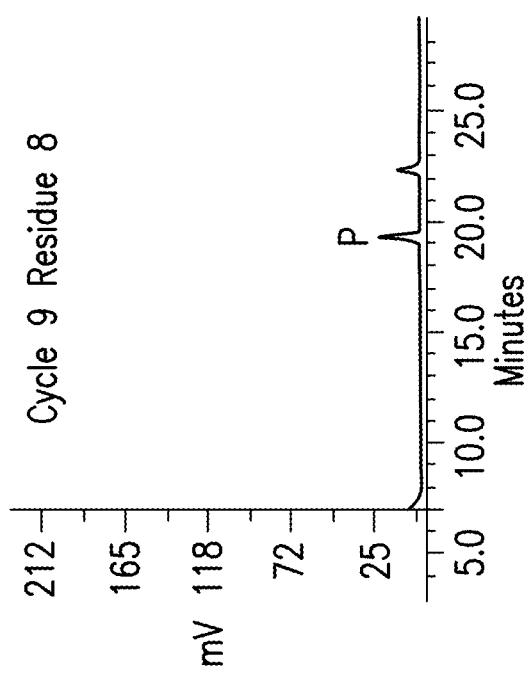
Figure 4I:

FIG. 4I is a schematic illustration of the various peptides that can be detected during the various cycles of N-terminal analysis. The peptide sequences are as follows:

THTCPPCPAPELLG, (SEQ ID NO: 1)

C-PTH, (SEQ ID NO: 2)
and

PPCPAPELLG. (SEQ ID NO: 3)

Figure 5C:
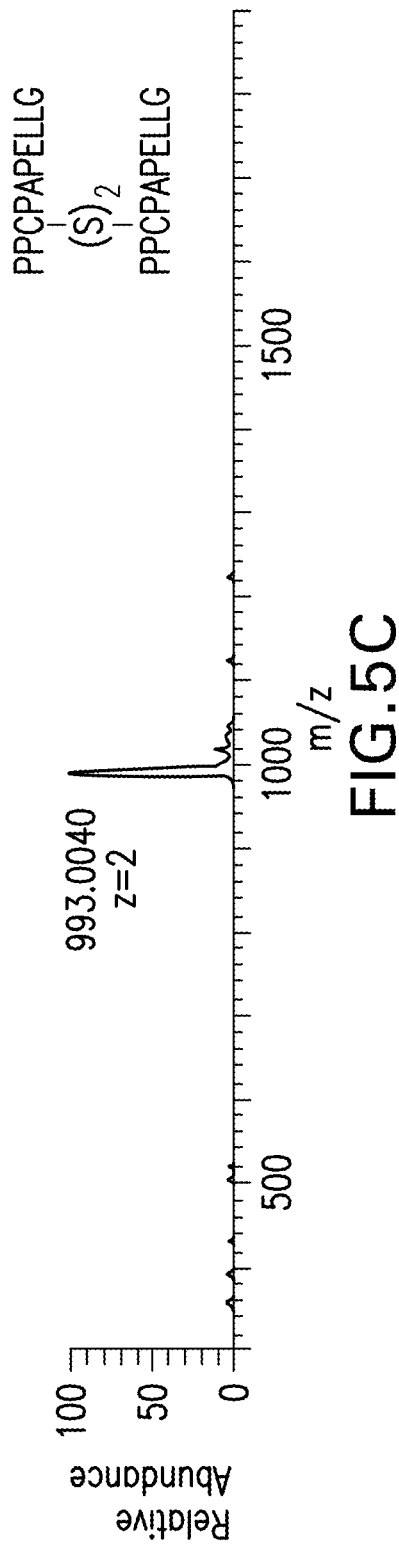
Figure 5D:
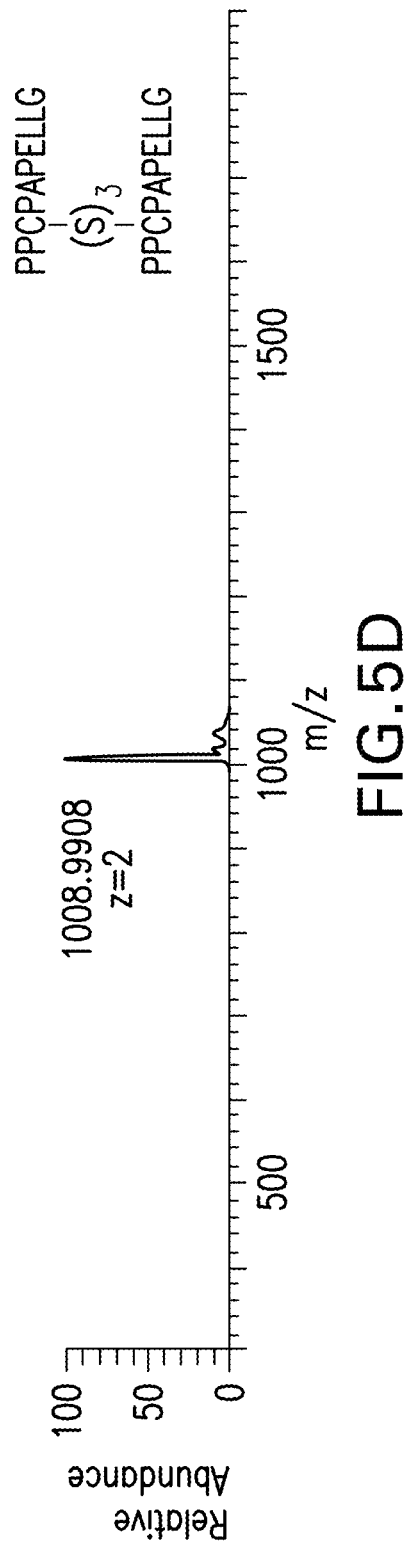
Figure 5E:
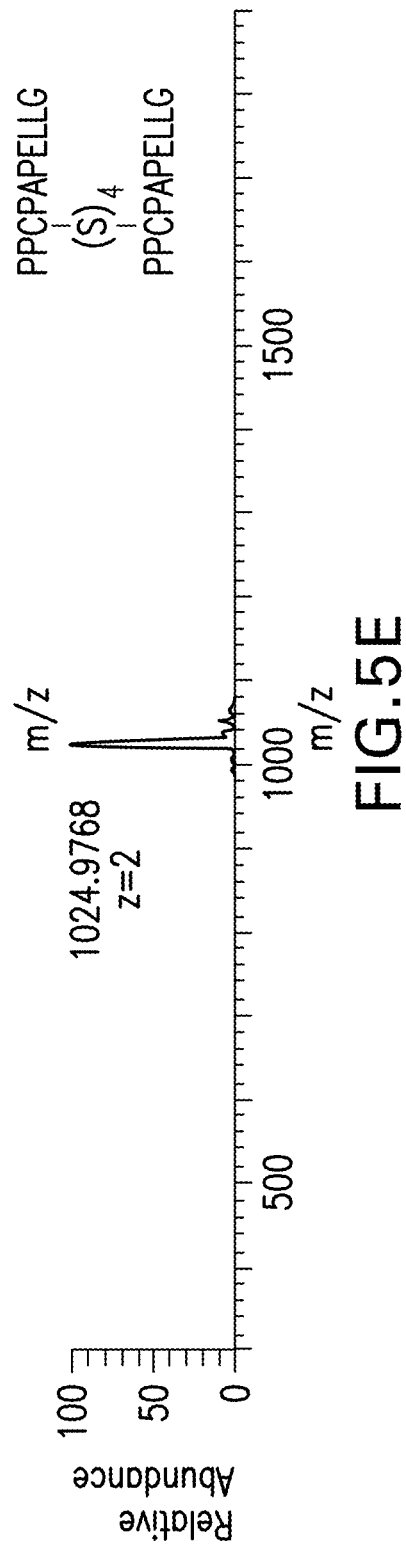
Figure 5F:
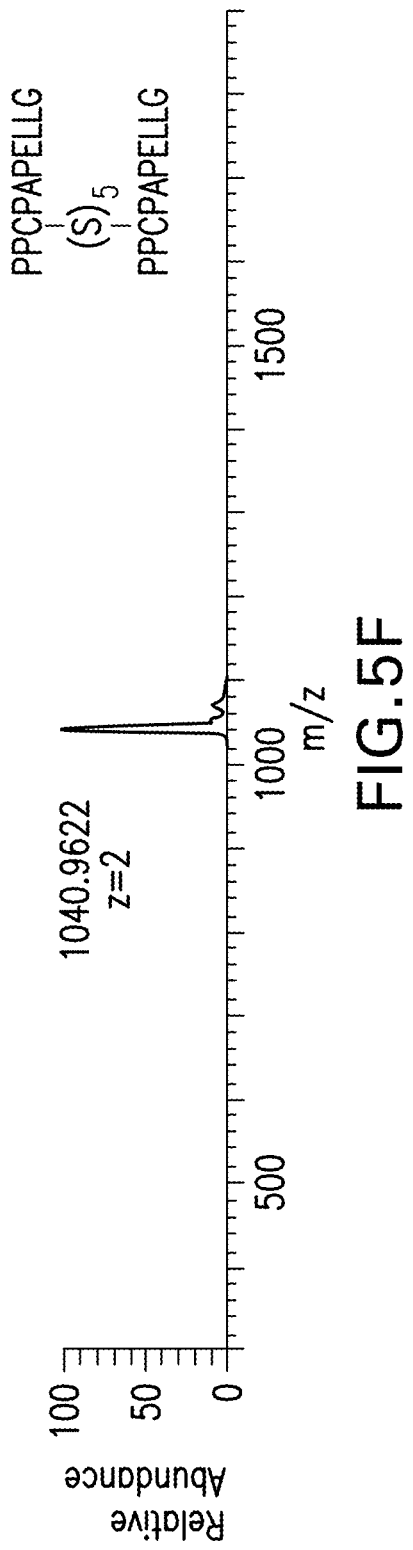

FIGS. 5A and 5B are chromatograms showing results from LC-MS analysis of the remaining peptides after four cycles of Edman degradation. FIG. 5A shows peptides with crossed disulfide bonds and FIG. 5B shows peptides with parallel disulfide bonds. FIG. 5C-5F are chromatograms of the individual peptides from FIG. 5A. The peptide sequences are as follows: C-PTH (SEQ ID NO:2) and PPCPAPELLG (SEQ ID NO:3).

Figure 6A:
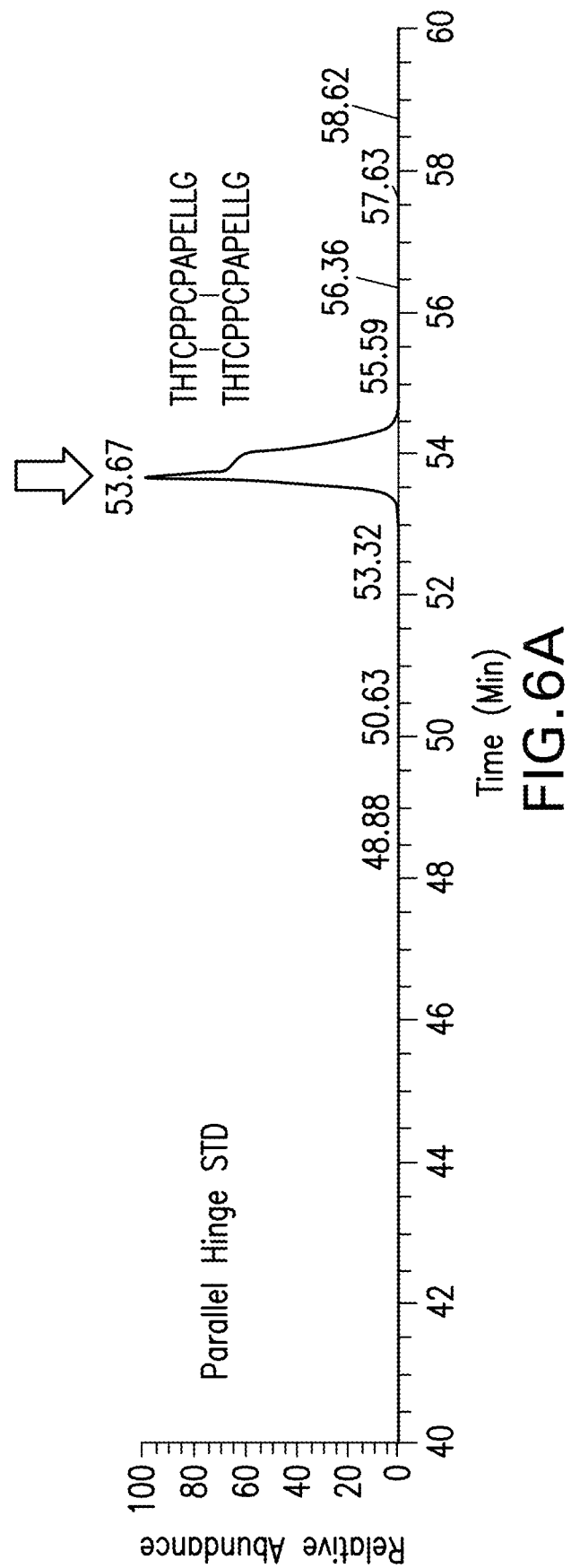
Figure 6B:
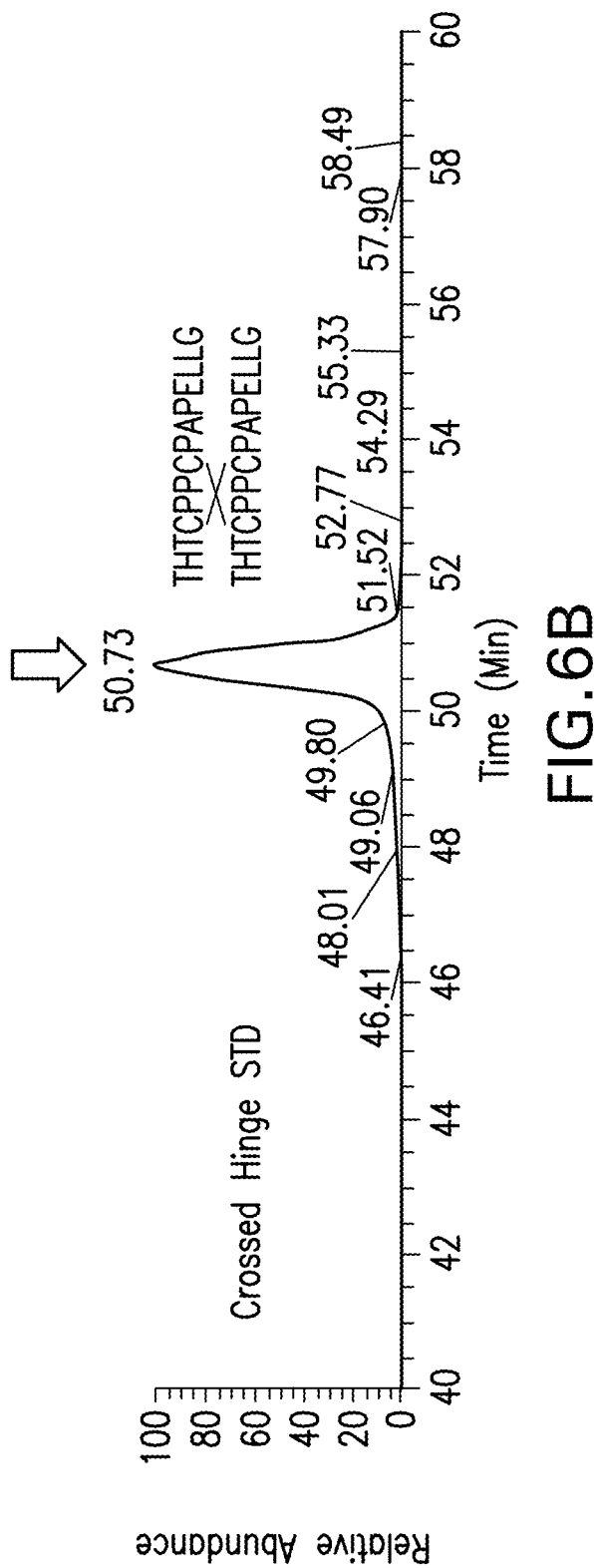
Figure 6C:
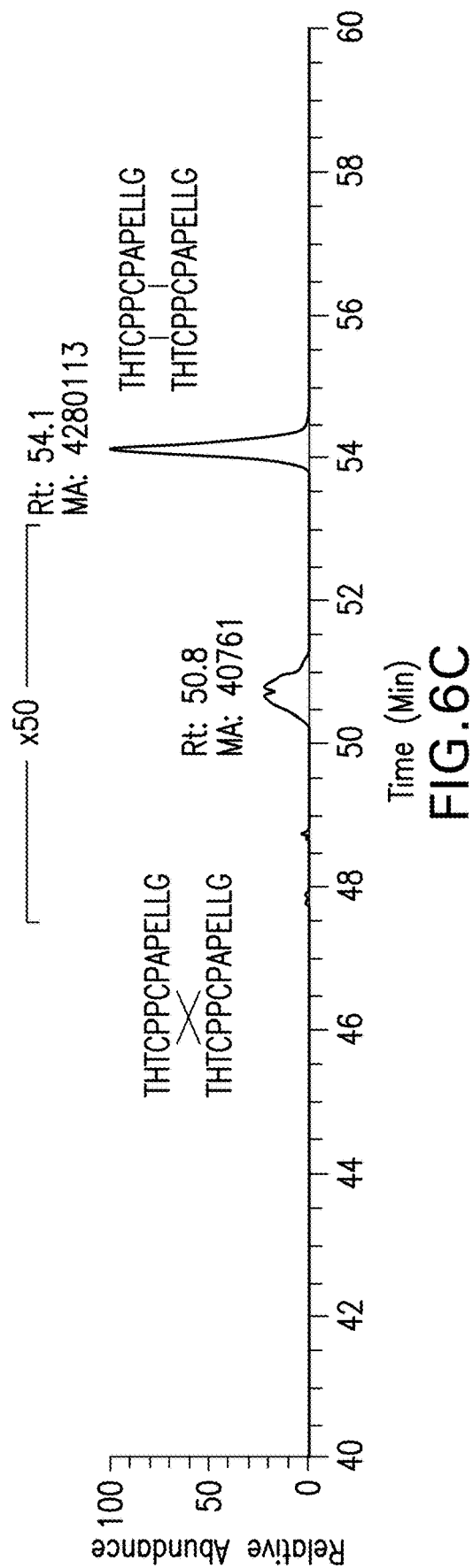

FIG. 6A is a chromatogram of a parallel hinge peptide standard for IgG1 mAb1. FIG. 6B is a chromatogram of a crossed hinge peptide standard for IgG1 mAb. FIG. 6C is a chromatogram of IgG1 mAb1 peptides. The X axis represent time (minutes) and the Y axis represents relative abundance. The peptides have the sequence THTCPPCPAPELLG (SEQ ID NO:1).

Figure 7A:
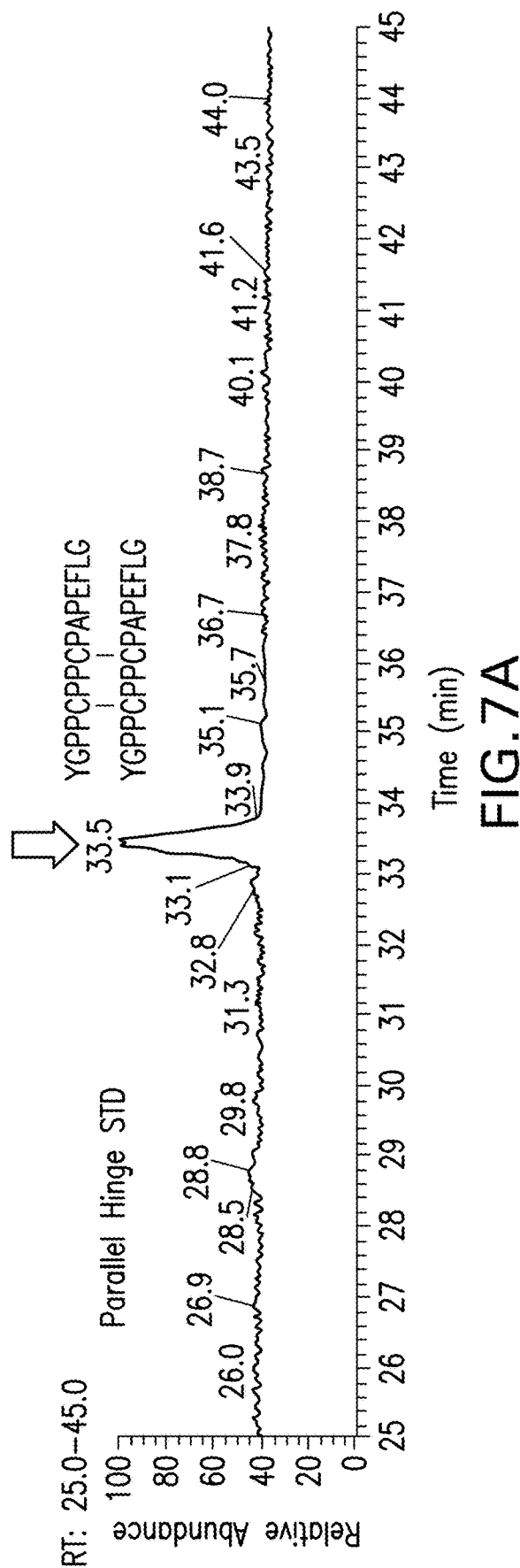
Figure 7B:
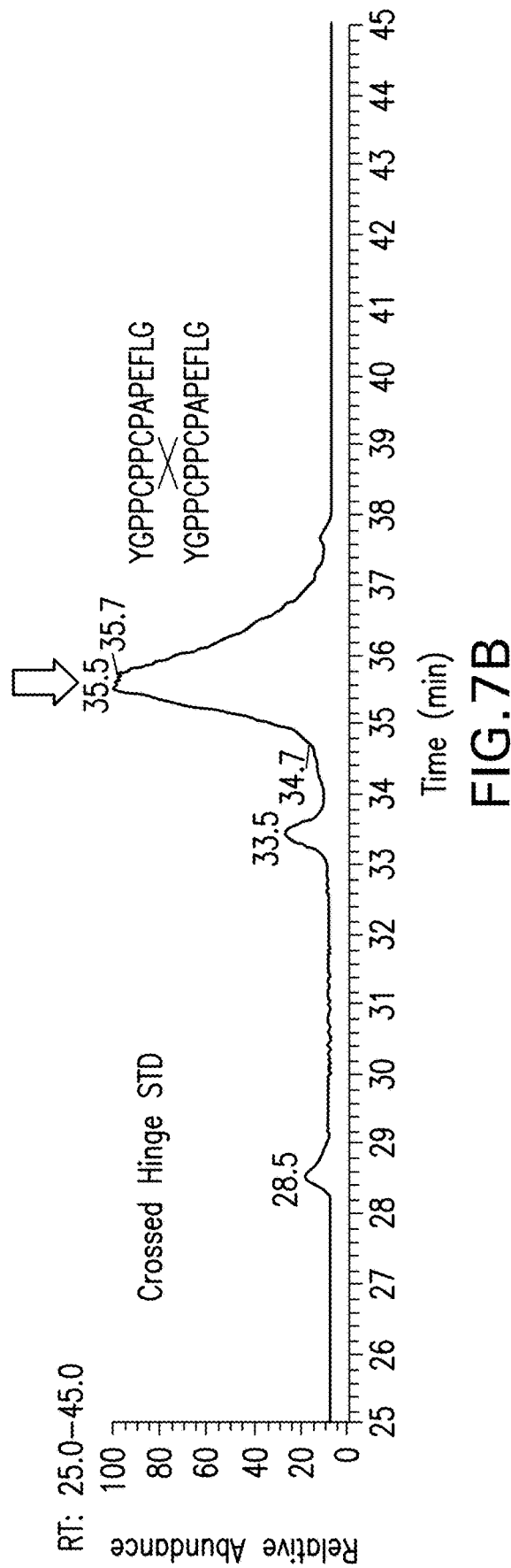

FIG. 7A is a chromatogram of a parallel hinge peptide standard for IgG4 mAb1. FIG. 7B is a chromatogram of a crossed hinge peptide standard for IgG4 mAb1. FIG. 7C is a chromatogram of IgG4 mAb1 peptides. The X axis represent time (minutes) and the Y axis represents relative abundance. The peptides have the sequence YGPPCPPCPAPEFLG (SEQ ID NO:4).

DETAILED DESCRIPTION OF THE INVENTION

I. Definitions

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by genetic engineering techniques (e.g., such as a sequence encoding a chimeric protein, or a codon-optimized sequence, an intronless sequence, etc.) where it may reside as an episome or be integrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in U.S. Pat. No. 8,586,713, which is incorporated by reference into this application.

"Hinge region" refers to the flexible amino acid stretch in the central part of the heavy chains of the IgG and IgA immunoglobulin classes, which links these 2 chains by disulfide bonds. In IgG immunoglobulins the hinge region is located between the CH1 and CH3 constant domains. The hinge region affords flexibility to the antibody, and allows easier binding to the antigen.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Rath, T., et al., *Crit Rev Biotech*, 35(2): 235-254 (2015), Levin, D., et al., *Trends Biotechnol*, 33(1): 27-34 (2015)) "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein comprises two or more distinct receptor chains that bind to one or more ligand(s). For example, an Fc-fusion protein is a trap, such as for example an IL-1 trap or VEGF trap.

The term "disulfide bond" refers to the linkage formed by the oxidation of two SH groups, each attached to a cysteine. Disulfide bonds play an important role in the folding and stability of many proteins. IgGs include two heavy chains (HC) and two light chains (LC) covalently linked by a total of 16 inter- or intra-molecular disulfide bonds. IgG mAbs contain 32 cysteine residues, 5 cysteine residues on each LC and 11 cysteine residues on each HC. Each LC contains one variable domain and one constant domain with a disulfide bond connection. The $5^{th}$ cysteine on the LC is linked to either the $3^{rd}$ or $5^{th}$ cysteine of the HC to form an interchain disulfide bond. The heavy chains include an N-terminal variable domain (VH) and three constant domains (CH1, CH2, and CH3) with a hinge region between CH1 and CH2 (Vidarsson, G., et al., *Front Immunol*, 5:520 (2014)). The 6th and 7th cysteine on each HC are bonded forming the hinge region. The hinge region of an immunoglobulin helps form the Y-shaped structure of the immunoglobulin molecule. The Y shape makes possible the flexibility of the immunoglobulin molecules required in antigen binding.

"Intra-chain disulfide bond" refers to bonds that are formed between two cysteines within the same protein chain.

"Inter-chain disulfide bond" refers to bonds that are formed between two cysteines of individual chains of the same protein or between two cysteines of distinct proteins.

"Scrambled disulfide bond" refers to a disulfide bond in which a cysteine bonds to a cysteine to which it does not normally bond. For example, cysteine X binds to cysteine Z instead of cysteine Y. Exemplary scrambled disulfide bonds include but not limited to crossed and intra-chain disulfide bonds.

Figure 1A:
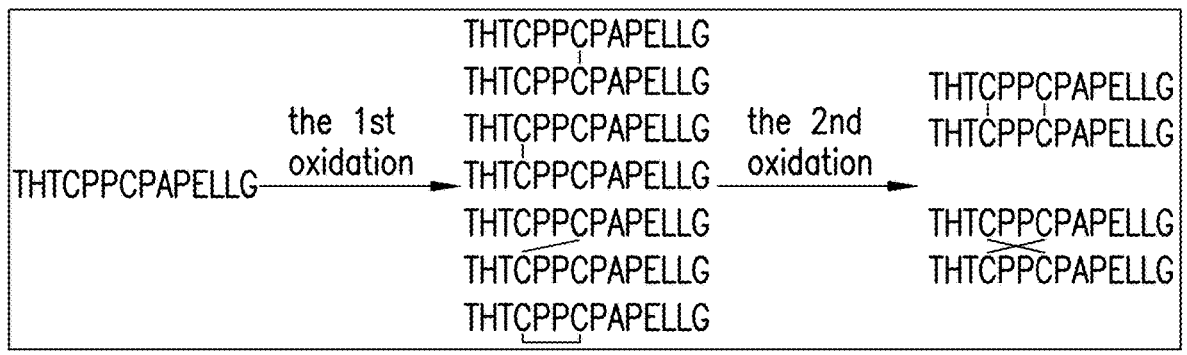
FIG. 1A is a schematic illustration showing the oxidation of a reduced hinge peptide having the sequence THTCPPCPAPELLG (SEQ ID NO:1).

As used herein, the term "crossed-hinge" refers to an antibody hinge region in which the disulfide bonds within the hinge region of the antibody are in a crossed instead of parallel formation as seen in the bottom right of FIG. 1A.

The term "LC-MS" refers to liquid chromatography-mass spectrometry which is an analytical chemistry technique that combines the physical separation capabilities of liquid chromatography (or HPLC) with the mass analysis capabilities of mass spectrometry (MS).

II. Methods of Characterizing Disulfide Bonds

Disulfide bonds are critical for IgG tertiary structure, stability, and biological function. Cysteine residues are involved in disulfide bonds. Each subclass of human IgG molecules has a well-defined homogenous disulfide structure; however, there are many reported cases in which disulfide bond heterogeneity exists. Any two cysteines in close proximity will form a covalent bond, even cysteines that do not naturally pair together. The formation of disulfide bonds between non-naturally paired cysteines is called scrambling or aggregation. Disclosed herein are different methods for identifying disulfide bonds. Also disclosed herein are methods for producing protein drug products with less than 30% scrambled disulfide bonds A. Characterizing Disulfide Bonds Analysis of disulfide bonds is important for quality control assessment of mAbs. In one embodiment, the disulfide bonds are in the hinge region. Traditional methods for mAb hinge region disulfide bond pattern analysis involves proteolysis, fractionation and Edman degradation analysis, which is time-consuming and labor-intensive. In addition, traditional methods such as $MS^2$-based techniques fail to distinguish between crossed and parallel hinge peptides. Identifying scrambled disulfide bonds is difficult because of the very low number of scrambled disulfide bonds that occur. Antibodies with scrambled disulfide bonds in the hinge region can be less stable and have a potential for inducing immunogenicity if administered to a subject. Disclosed herein are compositions and methods of use thereof for characterizing disulfide bonds in proteins, for example monoclonal antibodies. Peptide standards with native and scrambled disulfide bond patterns are provided herein. These peptide standards can be used in mass spectrometry analysis to focus the analysis on peptides that elute with the peptide standards. Methods of applying the disclosed peptide standards to hinge region disulfide bond characterization are also provided.

1. Peptide Standards for mAb Disulfide Bond Pattern Analysis

In one embodiment the peptide standard is formed by two peptides covalently bound together by one or more disulfide bonds. The scrambled disulfide bonds occur when a disulfide bond forms between two amino acids that are not directly opposite of each other. FIG. 7A shows the natural parallel disulfide bond. FIG. 7B shows an exemplary crossed disulfide bond also referred to as a scrambled disulfide bond. FIG. 1A shows parallel, crossed and intra-chain disulfide bonds. In one embodiment, the peptide standards can be used to identify the presence of parallel, crossed, or intra-chain disulfide bonds in a protein sample, for example scrambled disulfide bonds or native disulfide bonds in an antibody, for example a monoclonal antibody. In another embodiment, the peptide standards can detect intra-chain disulfide bonds in a protein or peptide. Further details for making and using the disclosed disulfide bond peptides are provided below.

i. Synthesis

One embodiment provides a method for synthesizing disulfide bond peptide standards. Peptide standards can be synthesized using techniques known in the art, including but not limited to liquid phase synthesis, solid phase peptide synthesis, and recombinant technology (Stawikowski, M., and Fields, G. B., *Current Protoc Protein Sci*, Chapter: Unit 18.1 (2002)).

The peptide standards can include fragments of the protein containing the disulfide bonds to be analyzed. The protein can be fragmented or sections of the protein containing the disulfide bonds to be analyzed can be synthesized and used to produce disulfide bond peptide standards. In some embodiments, the peptide standard sequence has 100% sequence identity to the region of the protein or protein drug product of interest that includes the disulfide bond. In other embodiments, the peptide standard sequence has at least 90% sequence identity to the region of the protein or protein drug product of interest that includes the disulfide bond. The peptide standard sequence can have 75%, 80%, 85%, 90%, 95%, 97%, 98%, or 99% sequence identity to the region of the protein or protein drug product of interest that includes the disulfide bond. In other embodiments, the sequence of the peptide standard only represents a portion of the region that includes the disulfide bond. The peptide standards are typically 5 to 20 amino acids in length.

The formation of disulfide bonds in the peptide standards can be induced through oxidation of cysteine residues in the peptide standard. Methods of forming disulfide bonds at cysteine include but are not limited to air oxidation, chemical oxidation, and exposing the peptide to copper ($Cu^{2+}$) or zinc. Air oxidation occurs by mixing thiol and cysteine containing peptides in buffer open to the air. In another embodiment, the formation of disulfides on a peptide can be accomplished by disulfide exchange, for example by using 5,5-dithiobis(2-nitrobenzoate) (DTNB or Ellman's Reagent). In one embodiment, other common chemicals for inducing oxidation of cysteine residues are activated reagents, including but not limited to iodine, sulfenyl halides, iodoacetamides, maleimides, benzylic halides and bromomethylketones. In another embodiment, disulfide bonds can be formed by exposing the peptide to copper or zinc. This can be achieved by using an inert platinum electrode or a sacrificial electrode (copper or zinc) or by generating metallic ions in electrospray ionization mass spectrometry (ESI-MS). In one embodiment, the molar ratio of peptide:$Cu^{2+}$ needed to induce the formation of disulfide bonds is 5:1 Higher peptide concentration can preferentially induce the formation of hinge dimers over the formation of intra-chain disulfide bonds.

The peptide standards can be exposed to $Cu^{2+}$ to induce single parallel or crossed disulfide bonds. In one embodiment, the peptide standards are oxidized for about 1 hour to about 6 hours. In a preferred embodiment, the peptide standards are oxidized for 2 hours. In another embodiment, the peptide standards can be oxidized for up to 24 hours in order to induce two or more parallel or crossed disulfide bonds.

ii. Authentication

In one embodiment, the characteristics of the synthesized peptide standards are determined. The characteristics include the retention time and m/z of each peptide standard. The synthesized peptide standards can be separated or fractionated using various chromatography methods. Peptide standards containing parallel disulfide bonds are distinguishable from peptide standards containing crossed or intra-chain disulfide bonds.

In one embodiment, N-terminal sequence analysis can be used to confirm the identity of the peptide standards. N-terminal sequence analysis involves a series of chemical reactions that derivatize and remove one amino acid at a time from the N-terminus of purified peptides or intact proteins. N-terminal analysis can detect disulfide bonds because the reaction to remove one amino acid at a time from the N-terminus does not disrupt the bonds between the cysteine residues in the disulfide bond.

In another embodiment, Edman degradation can be utilized to sequence the disulfide bond peptide standards. Edman degradation is similar to N-terminal analysis in that it detects the sequence of a protein or peptide in order by removing one amino acid at a time from the N-terminus of the protein or peptide. However, the first round of Edman degradation is often contaminated by impurities and therefore does not give an accurate determination of the N-terminal amino acid. Edman degradation can detect disulfide bonds because the reaction to remove one amino acid at a time from the N-terminus does not disrupt the bonds between the cysteine residues in the disulfide bond. In one embodiment, N-terminal analysis can be combined with Edman degradation to give a complete, ordered sequence of the synthesized disulfide bond peptide standards.

Other methods of sequencing peptides are considered. These include but are not limited to C-terminal analysis and mass spectrometry.

2. Methods for Characterizing Disulfide Bonds in the Hinge Region

One embodiment provides methods for identifying and characterizing disulfide bonds in a protein drug product. In another embodiment, the methods identify and characterize disulfide bonds specifically in the hinge region of an antibody. In one embodiment, the antibody is an IgG antibody. An exemplary method includes preparing scrambled disulfide bond peptide standards and native disulfide bond peptide standards according to the sequence of the protein drug product, cleaving a sample of protein drug product into peptides, analyzing the peptide standards and the protein drug product peptides, identifying scrambled and native disulfide bonds in peptides by comparing retention time, and quantifying the level of scrambled disulfide bond peptides. Detecting peptides having the same retention time or m/z as the peptide standard indicates that the type of disulfide bond in the peptide standard is present in the protein drug product.

i. Protein Sample Preparation

The protein or protein drug product of interest can be obtained for example from a bioreactor containing cells engineered to produce monoclonal antibodies.

In one embodiment, the protein or protein drug product of interest is digested into peptides. Methods of digesting proteins are known in the art. Proteins can be digested by enzymatic digestion with proteolytic enzymes or by non-enzymatic digestion with chemicals. Exemplary proteolytic enzymes for digesting proteins include but are not limited to trypsin, pepsin, chymotrypsin, thermolysin, papain, pronase, Arg-C, Asp-N, Glu-C, Lys-C, and Lys-N. Combinations of proteolytic enzymes can be used to ensure complete digestion. Exemplary chemicals for digesting proteins include but are not limited to formic acid, hydrochloric acid, acetic acid, cyanogen bromide, 2-nitro-5-thiocyanobenzoate, and hydroxyalamine.

In one embodiment, the protein drug product can be subjected to double digesting. In this embodiment, the first digestion can be performed using a broad-specificity protease, such as but not limited to proteinase K, thermolysin, substilisin, papain, chymotrypsin, or elastase. The second digestion can be performed using trypsin. In one embodiment, FabRICATOR® enzyme is used to digest the protein or protein drug product. FabRICATOR® enzyme digests antibodies at a specific site below the hinge therefore generating F(ab')2 and Fc/2 fragments. FabRICATOR® digestion can be combined with tryptic digestion.

ii. Hinge Region Disulfide Bond Pattern Analysis

The digested peptide mixture from the protein or protein drug product can be analyzed by liquid chromatography-mass spectrometry (LC-MS or LC-MS$^2$) to determine the mass of the digested peptides. In one embodiment, the digested peptide mixture is separated by liquid chromatography, for example size-exclusion chromatography.

The peptide mixture can then be analyzed using mass spectrometry. Methods of performing mass spectrometry are known in the art. See for example (Aeberssold, M., and Mann, M., *Nature,* 422:198-207 (2003)) Commonly utilized types of mass spectrometry include but are not limited to tandem mass spectrometry (MS/MS), electrospray ionization mass spectrometry, liquid chromatography-mass spectrometry (LC-MS), and Matrix-assisted laser desorption/ionization (MALDI). In another embodiment, selected reaction monitoring (SRM) is performed on the peptide mixture. In SRM, an ion of a particular mass is selected in the first stage of a tandem mass spectrometer and an ion product of fragmentation of the precursor ion is selected in the second mass spectrometer for detection.

In one embodiment, the hinge peptide standards are also analyzed. The standards are used to characterize the hinge region of the protein drug product of interest. In one embodiment, the retention time of the known hinge peptide standards are compared to the retention time of the peptide mixture from the protein drug product of interest. Detecting peptides having the same retention time or m/z as the peptide standard indicates that the type of disulfide bond in the peptide standard is present in the protein drug product.

B. Proteins of Interest

In one embodiment the protein of interest is a protein drug product or is a protein of interest suitable for expression in prokaryotic or eukaryotic cells. For example, the protein can be an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins in the complexes may be simple polypeptides consisting of a single subunit, or complex multisubunit proteins comprising two or more subunits. The protein of interest may be a biopharmaceutical product, food additive or preservative, or any protein product subject to purification and quality standards In some embodiments, the protein of interest is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a dual-specific, tetravalent immunoglobulin G-like molecule, termed dual variable domain immunoglobulin (DVD-IG), an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In another embodiment, the antibody comprises a chimeric hinge. In still other embodiments, the antibody comprises a chimeric Fc. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g., an anti-PD1 antibody as described in U.S. Pat. Appln. Pub. No. US2015/0203579A1), an anti-Programmed Cell Death Ligand-1 (e.g., an anti-PD-L1 antibody as described in in U.S. Pat. Appln. Pub. No. US2015/0203580A1), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPt13 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-05 antibody as described in U.S. Pat. Appln. Pub. No US2015/0313194A1), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g., an anti-PCSK9 antibody as described in U.S. Pat. No. 8,062,640 or U.S. Pat. No. 9,540,449), an Anti-Growth and Differentiation Factor-8 antibody (e.g. an anti-GDF8 antibody, also known as anti-myostatin antibody, as described in U.S. Pat. No. 8,871,209 or 9,260,515), an anti-Glucagon Receptor (e.g. anti-GCGR antibody as described in U.S. Pat. Appln. Pub. Nos. US2015/0337045A1 or US2016/0075778A1), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat. No. 8,735,095 or 8,945,559), an anti-interleukin 6 receptor antibody (e.g., an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. No. 9,453,072 or 9,637,535), an anti-Respiratory syncytial virus antibody (e.g., anti-RSV antibody as described in U.S. Pat. No. 9,447,173), an anti-Cluster of differentiation 3 (e.g., an anti-CD3 antibody, as described in U.S. Pat. Nos. 9,447,173 and 9,447,173, and in U.S. Application No. 62/222,605), an anti-Cluster of differentiation 20 (e.g., an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in U.S. Pat. Appln. Pub. No. US2015/0337029A1), an anti-Ebola virus antibody (e.g. as described in U.S. Pat. Appln. Pub. No. US2016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g. an anti-NGF antibody as described in U.S. Pat. Appln. Pub. No. US2016/0017029 and U.S. Pat. Nos. 8,309,088 and 9,353,176) and an anti-Protein Y antibody. In some embodiments, the bispecific antibody is selected from the group consisting of an anti-CD3 x anti-CD20 bispecific antibody (as described in U.S. Pat. Appln. Pub. Nos. US2014/0088295A1 and US20150266966A1), an anti-CD3 x anti-Mucin 16 bispecific antibody (e.g., an anti-CD3 x anti-Muc16 bispecific antibody), and an anti-CD3 x anti-Prostate-specific membrane antigen bispecific antibody (e.g., an anti-CD3 x anti-PSMA bispecific antibody). In some embodiments, the protein of interest is selected from the group consisting of abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the 11-1R1 extracellular region fused to Fc of hIgG1; see U.S. Pat. No. 6,927,004, which is herein incorporated by reference in its entirety), or a VEGF trap (e.g., aflibercept or ziv-aflibercept, which comprises the Ig domain 2 of the VEGF receptor Flt1 fused to the Ig domain 3 of the VEGF receptor Flk1 fused to Fc of hIgG1; see U.S. Pat. Nos. 7,087,411 and 7,279,159). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

C. Producing mAb with Native Disulfide Bond Pattern

One embodiment provides methods of producing a protein drug product containing less than 30% scrambled disulfide bonds. An exemplary method includes culturing cells producing the antibody in a cell culture under suitable conditions to produce the antibody, purifying the antibody under suitable conditions to extract the antibody, admixing the antibody with excipients under suitable conditions to stabilize the antibody, obtaining a sample of the antibody from the cell culture, following purification of the antibody from the cell culture, or following the addition of excipients to the purified antibody, characterizing disulfide bonds of the antibody according to the disclosed methods, and modifying one or more cell culture, purification or excipient conditions to reduce the amount of crossed hinge disulfide bonds of the antibody.

The one or more cell culture, purification, or excipient conditions that are changed to reduce the amount of scrambled disulfide bonds in the antibody include but are not limited to temperature, pH, oxygen levels, reactive oxygen species, surfactants, or combinations thereof. In one embodiment, an amino acid free strategy of cell culture could affect disulfide bond formation.

In one embodiment, the cells producing the antibody are Chinese hamster ovary cells. In another embodiment, the cells are hybridoma cells.

In one embodiment, the protein drug product can have less than 30% scrambled disulfide bonds in the hinge region. The protein drug product can have less than 30%, 25%, 20%, 18%, 16%, 14%, 12%, 10%, 9%, 8%, 7%, 6%, 5%, 4%, 3%, 1%, 0.5%, or 0.1% scrambled disulfide bonds in the hinge region.

In another embodiment, the protein drug product can have less than 10% scrambled disulfide bonds overall. The protein drug product can have less than 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, 0.5%, or 0.1% scrambled disulfide bonds.

EXAMPLES

Example 1: Synthesis of Parallel and Crossed Hinge Peptides

Methods:

Cross-Linking

Cysteine containing peptides were purchased from a commercial vendor. The peptides were cross-linked by incubation with 1 mM $Cu^{2+}$ as the oxidant in the presence of air. The molar ratio of peptide to $Cu^{2+}$ was 5:1.

N-Terminal Analysis/Edman Degradation

The cross-linked peptides were suspended in water and were placed into a protein sequencer. The peptides were exposed to phenyl isothiocyanate (PITC). PITC couples with the N-terminal residue to form a PTC polypeptide. Trifluoroacetic acid was added to the reaction and the PTC N-terminal residue underwent acid cleavage, resulting in the release of an unstable ATZ-amino acid. The ATZ-amino acid was separated from the peptide solution into a conversion flask containing ethyl acetate. The ATZ-amino acid was converted into a stable PTH-amino acid with 25% TFA, v/v in water. The PTH-amino acid solution was injected onto an HPLC. Each amino acid of the peptide is identified by HPLC.

Figure 1B:
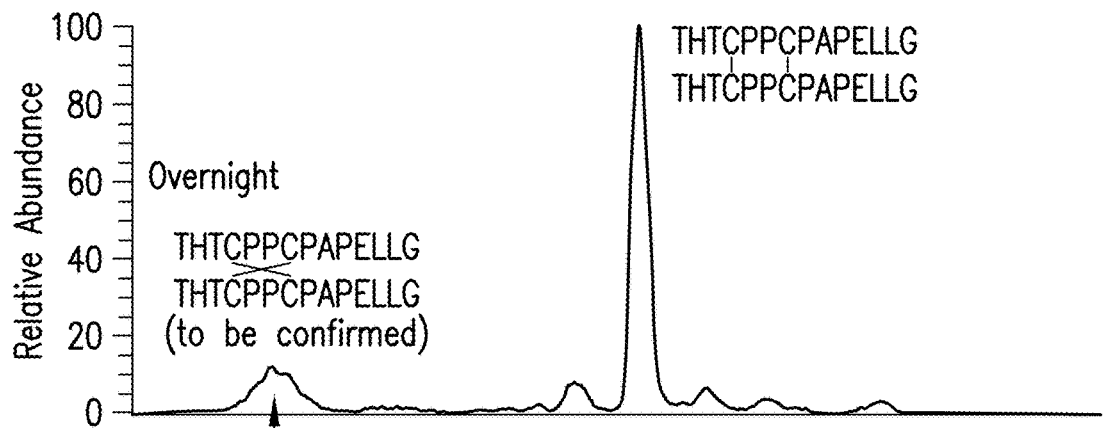
FIG. 1B is a chromatogram showing hinge peptides that were oxidized overnight, resulting in peptides with two crossed disulfide bonds and hinge peptides with two parallel disulfide bonds. The peptides have the sequence THTCPPCPAPELLG (SEQ ID NO:1).
Figure 1C:
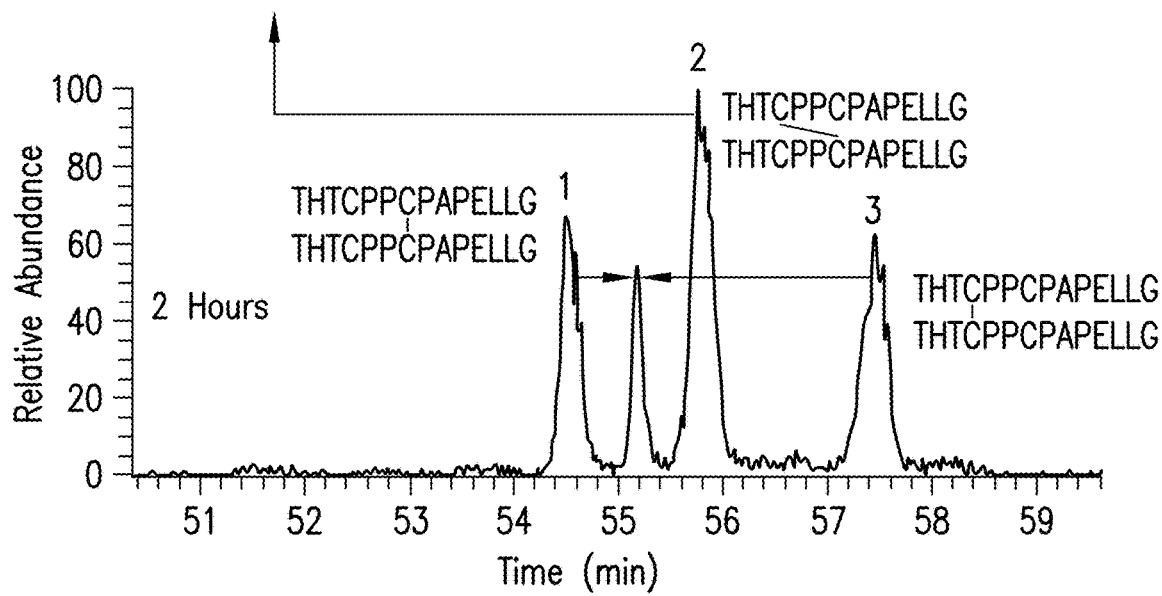
FIG. 1C is a chromatogram showing peptides with one parallel (Peak 1 and 3) or crossed (Peak 2) disulfide bond. The X axis represents time (minutes) and the Y axis represents abundance.
Figure 3H:
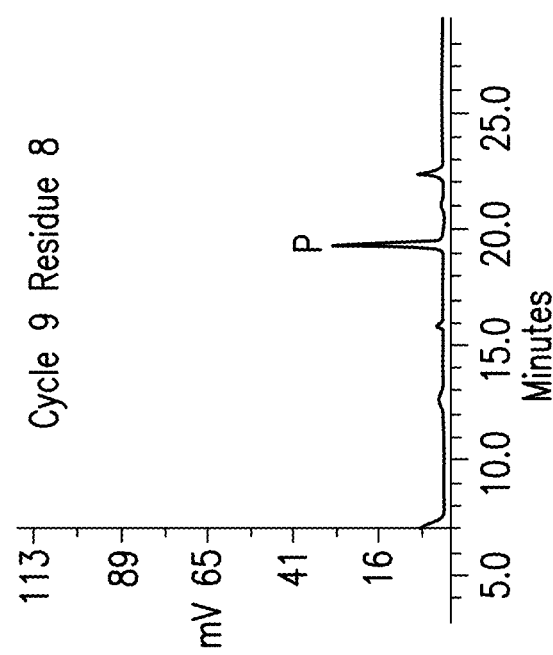
Figure 3I:
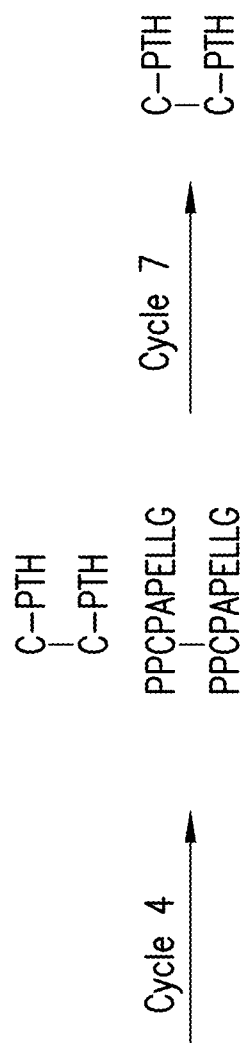
FIG. 3I is a schematic illustration of the various peptides that can be detected during the cycles of N-terminal analysis.

Results $Cu^{2+}$ has been reported to induce the formation of disulfide bonds by producing radicals (Prudent, M., and Girault, H. H., *Metallomics*, 1:157-165 (2009)). Peptides exposed to $Cu^{2+}$ at a molar ratio of peptide/$Cu^{2+}$ of 5/1 formed disulfide bonds as illustrated in FIG. 1A. The first oxidation formed a single, non-selective bond that was either parallel or crossed in nature (FIGS. 1A and 1C). During the second disulfide bond formation, parallel connectivity was found to be the preferred connection (FIG. 1B). The peptide concentration was found to affect the type of disulfide bond that was formed. A higher concentration of peptide, 8 μg/ml, induced the formation of more parallel hinge dimers than a concentration of 0.1 μg/ml (FIGS. 2A-2B). Higher peptide concentration favors inter-molecular bridges.

The identity of the peptides was confirmed using N-terminal analysis and Edman degradation (FIGS. 3A-3I, FIGS. 4A-4I, and FIGS. 5A-5B).

Example 2: Analysis of the Hinge Region of Two mAbs

Methods
Hinge DSB Characterization

Antibodies were first digested into peptides. IgG1 antibodies were subjected to dual-enzyme digestion using proteinase K followed by trypsin. IgG4 antibodies were subjected to digestion by FabRICATOR followed by trypsin. Hinge peptide standards were prepared as above, using the hinge region sequence of the IgG1 and IgG4 antibodies to prepare the peptides. The digested peptide mixtures were subjected to LC-MS analysis. Hinge peptide standards were also subjected to LC-MA analysis. Retention time analysis was performed to compare the retention time of the antibody peptides to the retention time of the hinge peptide standards.

Results

IgG1 mAb1 was subjected to digestion into peptides and the resulting peptides were subjected to LC/MS analysis. The hinge peptide standards described above were also subjected to LC/MS analysis. As shown in FIGS. 6A-6C, IgG1 mAb1 has about 0.9% crossed hinge disulfide bonds.

A second antibody, IgG4 mAb1, was also analyzed using the disclosed methods and hinge disulfide bond peptide standards. As shown in FIGS. 7A-7C, IgG4 mAb1 had about 0.6% crossed hinge disulfide bonds.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A method of producing a protein drug product, comprising:
    producing the protein drug product in a cell culture;
    identifying scrambled disulfide bonds of the protein drug product, wherein identifying the scrambled disulfide bonds of the protein drug product comprises: preparing peptide standards comprising regions of the protein drug product containing one or more disulfide bonds, wherein the disulfide bonds in the peptide standards are formed through an oxidation reaction that comprises exposing the peptide standard to zinc; and
    modifying one or more cell culture, purification or excipient conditions to reduce the amount of crossed hinge disulfide bonds of the protein drug product to less than 1.0%.

2. The method of claim 1, wherein the one or more cell culture, purification or excipient conditions that are modified are selected from the group consisting of temperature, pH, oxygen levels, reactive oxygen species, surfactants, or combinations thereof.

3. The method of claim 1, wherein the protein drug product is selected from the group consisting of an antibody, a fusion protein, recombinant protein, or a combination thereof.

4. The method of claim 1, wherein preparing the peptide standards comprises using a peptide concentration of from 0.1 μg/mL to 0.8 μg/mL.

5. The method of claim 1, wherein the disulfide bonds in the peptide standards are formed through an oxidation reaction that comprises oxidation by air or chemical.

6. The method of claim 1, wherein the disulfide bonds in the peptide standards are formed through an oxidation reaction that comprises oxidation with $Cu^{2+}$.

7. The method of claim 6, wherein the molar ratio of peptide:$Cu^{2+}$ for formation of disulfide bonds is 5:1.

8. The method of claim 1, wherein a first peptide standard comprises a first scrambled disulfide bond, and a second standard comprises a second and different scrambled disulfide bond.

9. The method of claim 8, wherein the first peptide standard and the second peptide standard have different liquid chromatography retention times.

10. The method of claim 1, wherein identifying the scrambled disulfide bonds of the product drug product further comprises:
    digesting a sample of the protein drug product into peptides;
    analyzing a sample containing the protein drug product peptides comprising one or more disulfide bonds and the peptide standards comprising one or more disulfide bonds using an LC-MS2 system; and
    comparing retention times of the sample containing protein drug product peptides comprising one or more disulfide bonds with the retention times of the peptide standards comprising one or more disulfide bonds.

11. The method of claim 10, wherein peptides detected at the retention time of the first peptide standard indicates that the scrambled disulfide bonds of the first peptide standard are present in the protein drug product, and peptides detected at the retention time of the second peptide standard indicates that the scrambled disulfide bonds of the second peptide standard are present in the protein drug product.

12. The method of claim 10, wherein digesting the sample comprises tryptic digestion or dual-enzyme digestion.

13. The method of claim 1, wherein the scrambled disulfide bonds are selected from the group consisting of crossed disulfide bonds, crisscrossed disulfide bonds, and intra-chain disulfide bonds.

14. The method of claim 1, wherein the one or more disulfide bonds are in the hinge region of an antibody.

15. The method of claim 1, wherein the method further comprises:
    quantifying the amount of one or more disulfide bonds present in the protein drug product.

16. The method of claim 3, wherein the protein drug product is a fusion protein.

17. The method of claim 16, wherein the fusion protein is an Fc fusion protein.

18. The method of claim 1, wherein the protein drug product has less than 30% scrambled disulfide bonds.

* * * * *

```
                         SEQUENCE LISTING

Sequence total quantity: 4
SEQ ID NO: 1            moltype = AA  length = 14
FEATURE                 Location/Qualifiers
REGION                  1..14
                        note = Peptide standard
source                  1..14
                        mol_type = protein
                        organism = synthetic construct
SEQUENCE: 1
THTCPPCPAP ELLG                                                         14

SEQ ID NO: 2            moltype = AA  length = 4
FEATURE                 Location/Qualifiers
REGION                  1..4
                        note = Peptide standard
source                  1..4
                        mol_type = protein
                        organism = synthetic construct
SEQUENCE: 2
CPTH                                                                    4

SEQ ID NO: 3            moltype = AA  length = 10
FEATURE                 Location/Qualifiers
REGION                  1..10
                        note = Peptide standard
source                  1..10
                        mol_type = protein
                        organism = synthetic construct
SEQUENCE: 3
PPCPAPELLG                                                              10

SEQ ID NO: 4            moltype = AA  length = 15
FEATURE                 Location/Qualifiers
REGION                  1..15
                        note = Peptide standard
source                  1..15
                        mol_type = protein
                        organism = synthetic construct
SEQUENCE: 4
YGPPCPPCPA PEFLG                                                        15
```